(12) United States Patent
Ikuno

(10) Patent No.: US 9,598,297 B2
(45) Date of Patent: *Mar. 21, 2017

(54) METHOD FOR TREATING ORGANIC-MATTER-CONTAINING WATER

(75) Inventor: Nozomu Ikuno, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 996 days.

This patent is subject to a terminal disclaimer.

(21) Appl. No.: 13/138,248

(22) PCT Filed: Jan. 20, 2010

(86) PCT No.: PCT/JP2010/050607
§ 371 (c)(1),
(2), (4) Date: Jul. 22, 2011

(87) PCT Pub. No.: WO2010/098158
PCT Pub. Date: Sep. 2, 2010

(65) Prior Publication Data
US 2011/0297614 A1    Dec. 8, 2011

(30) Foreign Application Priority Data
Feb. 27, 2009 (JP) ................... 2009-046619

(51) Int. Cl.
*C02F 1/28* (2006.01)
*C02F 1/32* (2006.01)
(Continued)

(52) U.S. Cl.
CPC ............... *C02F 9/00* (2013.01); *A01N 59/00* (2013.01); *B01D 65/08* (2013.01); *C02F 1/283* (2013.01);
(Continued)

(58) Field of Classification Search
CPC ........ A01N 41/08; A01N 43/64; A01N 59/00; A01N 59/02; A01N 2300/00; B01D 61/04;
(Continued)

(56) References Cited

U.S. PATENT DOCUMENTS 3,101,318 A * 8/1963 Watson .................. C02F 1/283
                                                    210/778
3,170,883 A * 2/1965 Owen et al. ............. 252/186.36
(Continued)

FOREIGN PATENT DOCUMENTS

CN    1406484 A    4/2003
CN    1906132 A    1/2007
(Continued)

OTHER PUBLICATIONS

Chinese Patent Office, "Office Action for CN 201080003945.9", Mar. 28, 2013.
(Continued)

*Primary Examiner* — Joseph Drodge
(74) *Attorney, Agent, or Firm* — Manabu Kanesaka

(57) ABSTRACT

Disclosed is a treatment apparatus capable of inhibiting growth of microorganisms and carrying out long-term stable treatment in an activated carbon tower and a reverse osmosis membrane separation device during processes including activated carbon treatment and RO membrane separation treatment of a later step in a system for manufacturing ultrapure water used in an electronic device factory. A method for treating organic-matter-containing water includes: the slime-controlling-agent-adding step of adding a slime-controlling agent to organic-matter-containing water; the activated-carbon-treating step of treating with activated carbon the organic-matter-containing water having undergone the slime-controlling-agent-adding step; and the
(Continued)

reverse-osmosis-membrane-separation step of passing the organic-matter-containing water having undergone the activated-carbon-treating step through means for reverse osmosis membrane separation, wherein the slime-controlling agent uses a combined chlorine agent produced from a chlorine-based oxidizer and a sulfamic acid compound.

9 Claims, 3 Drawing Sheets

(51) Int. Cl.
| | |
|---|---|
| C02F 1/66 | (2006.01) |
| C02F 1/76 | (2006.01) |
| B01D 65/08 | (2006.01) |
| A01N 41/08 | (2006.01) |
| A01N 43/64 | (2006.01) |
| A01N 59/02 | (2006.01) |
| C02F 9/00 | (2006.01) |
| C02F 5/00 | (2006.01) |
| A01N 59/00 | (2006.01) |
| C02F 1/44 | (2006.01) |
| C02F 103/04 | (2006.01) |
| C02F 103/34 | (2006.01) |

(52) U.S. Cl.
CPC ............... C02F 1/32 (2013.01); C02F 1/441 (2013.01); C02F 1/66 (2013.01); C02F 1/76 (2013.01); C02F 5/00 (2013.01); C02F 2103/04 (2013.01); C02F 2103/346 (2013.01); C02F 2209/29 (2013.01)

(58) Field of Classification Search
CPC ... B01D 65/08; B01D 2311/04; B01D 2311/12; B01D 2311/2626; B01D 2311/2634; B01D 2311/2642; C02F 1/28; C02F 1/283; C02F 1/32; C02F 1/66; C02F 1/76; C02F 1/766; C02F 5/00; C02F 9/00; C02F 2103/04; C02F 2103/346; C02F 2209/29; C02F 2303/20; C02F 2303/22
USPC .... 210/202, 259, 263, 321.6, 639, 652, 663, 210/669, 679, 743, 754, 756, 764, 806, 210/636; 252/175, 176; 424/405
See application file for complete search history.

(56) References Cited

U.S. PATENT DOCUMENTS

| | | | | |
|---|---|---|---|---|
| 4,724,079 | A | * | 2/1988 | Sale et al. ............... 210/638 |
| 5,259,972 | A | * | 11/1993 | Miyamaru ........... B01D 61/025 |
| | | | | 210/195.2 |
| 6,398,965 | B1 | * | 6/2002 | Arba et al. ............... 210/652 |
| 6,461,514 | B1 | * | 10/2002 | Al-Samadi ............... 210/652 |
| 6,478,972 | B1 | * | 11/2002 | Shim ..................... A01N 59/00 |
| | | | | 162/161 |
| 6,858,145 | B2 | * | 2/2005 | Dey et al. ............... 210/640 |
| 7,186,344 | B2 | * | 3/2007 | Hughes .................... 210/652 |
| 7,285,221 | B2 | * | 10/2007 | Tsuneki ................ A01N 59/00 |
| | | | | 162/161 |
| 2003/0057155 | A1 | * | 3/2003 | Husain et al. ............ 210/636 |
| 2008/0173583 | A1 | * | 7/2008 | Boodoo et al. ........... 210/652 |

FOREIGN PATENT DOCUMENTS

| | | |
|---|---|---|
| CN | 101007664 A | 8/2007 |
| JP | H05-64782 | 3/1993 |
| JP | 2002-336886 | 11/2002 |
| JP | 2004-267830 | 9/2004 |
| JP | 2005-169372 | 6/2005 |
| JP | 2006-263510 | 10/2006 |
| JP | 3906855 | 1/2007 |
| TW | 2007-40704 A | 11/2007 |
| TW | 1318617 B | 12/2009 |
| TW | 1337982 B | 3/2011 |

OTHER PUBLICATIONS

Taiwan Patent Office, "Office Action for TW 99104170," Jul. 3, 2014.
China Patent Office, "Office Action for CN 201080003945.9," Feb. 4, 2015.

* cited by examiner

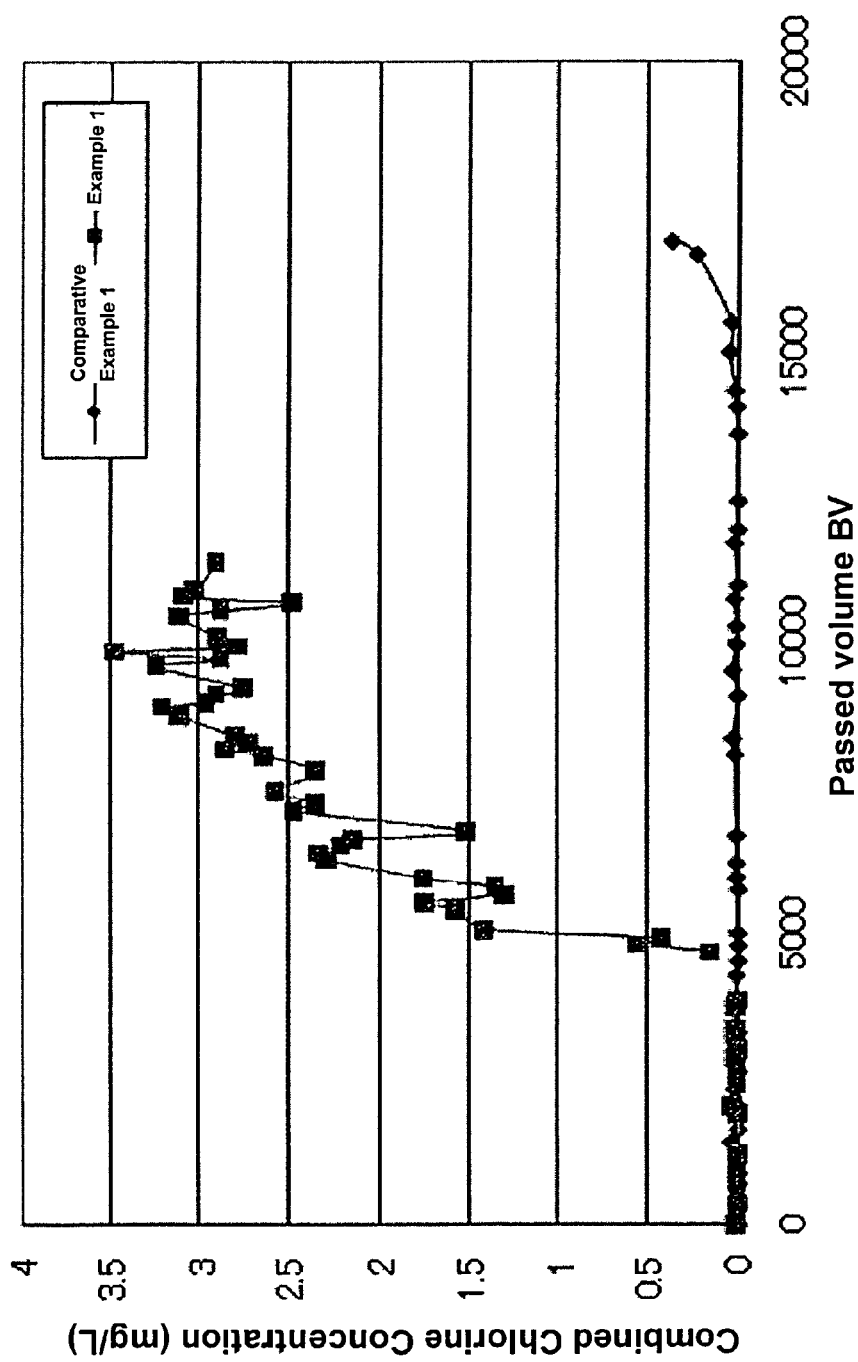

METHOD FOR TREATING ORGANIC-MATTER-CONTAINING WATER

FIELD OF INVENTION

The present invention relates to a method for treating organic-matter-containing water by using a slime-controlling agent. In a system for manufacturing ultrapure water used in an electronic device factory or in a system for treating and collecting high-concentration and low-concentration organic-matter (TOC)-containing drainage drained from the electronic device factory by using a membrane separation device utilizing a reverse osmosis (RO) membrane, the present invention relates to, in particular, a method for treating organic-matter-containing water, including preventing a decrease in flux in an RO membrane separation device due to membrane surface attachment of organic matter (i.e., organic matter fouling) or preventing a decrease in flux due to biofouling to carry out long-term stable treatment and simultaneously yield high-quality treated water by efficiently decreasing the TOC concentration in water.

BACKGROUND OF INVENTION

In an electronic device factory, ultrapure water is used as flushing water. The ultrapure water is generally manufactured by processes including activated carbon treatment and RO membrane separation treatment of a later step using, as raw water, industrial water or drainage drained from a factory.

The purposes of the activated carbon treatment are to remove an oxidizer in the raw water or to remove organic matter and chromaticity, etc.

Since organic matter is absorbed and enriched in an activated carbon tower, the inside of the activated carbon tower becomes an environment in which microorganisms readily proliferate by using the organic matter as a nutritional source. Generally speaking, microorganisms cannot be present under the presence of an oxidizer. Consequently, the microorganisms do not exist in water flowing into activated carbon that is exposed to the oxidizer. However, the mechanism of removing the oxidizer from the activated carbon is involved with a catalytic degradation reaction on the surface of the activated carbon. The reaction proceeds at the upper part in the tower, leading to a situation where the oxidizer fails to be present in the middle and lower parts in the activated carbon tower. Thus, the inside of the activated carbon tower becomes a hotbed for microorganisms, and about $10^3$ cells/ml to $10^7$ cells/ml of the cells typically leak from the activated carbon tower.

The activated carbon tower is an indispensable apparatus for manufacturing ultrapure water as means for removing an oxidizer and for removing organic matter. However, as described above, the tower could be a hotbed for microorganisms. Accordingly, there has been a problem that when the concentration of the organic matter flowing into the activated carbon tower is high, the microorganisms flowing out from the activated carbon tower cause biofouling of a safety filter or RO membrane installed in a later step, thereby being clogged.

In order to achieve sterilization in the activated carbon tower, methods utilizing hot water sterilization or chlorine sterilization have been carried out.

The hot water sterilization is a method for passing hot water having a temperature of 80° C. or more through an activated carbon tower for one hour or more, thereby maintaining the hot water. However, this method is required to flow and maintain high-temperature hot water for a prolonged period, and thus cannot be said to be an industrially advantageous method.

Regarding the chlorine sterilization, Japanese Patent Publication H5-64782A has proposed a method including back washing by adding NaClO to back washing water. However, in this method, NaClO is going to be degraded at the surface of the lower layer of an activated carbon tower into which the back washing water flows, so that NaClO does not prevail in the entire portion of the activated carbon tower. Therefore, a sufficient sterilization effect cannot be achieved.

Recently, the environmental standard and water-quality standard have tended to increasingly become strict. It has been desired to highly purify even final effluent. In addition, for the purpose of dissolving water shortage, it has also been desired to develop a high-level technique for treating water so as to collect and regenerate various drainage.

RO membrane separation treatment enables impurities (e.g., ions, organic matter, microparticles) in water to be effectively removed. Thus, recently, the treatment has been used in a large number of fields. For example, when high-concentration TOC- or low-concentration TOC-containing drainage including acetone and isopropyl alcohol, which are drained from processes for manufacturing a semiconductor is collected and reused, a method (e.g., Japanese Patent Publication 2002-336886A) has been widely adopted, in which the drainage is first biologically treated to remove the TOC components and the biologically treated water is subjected to RO membrane treatment to be purified.

However, when the biologically treated drainage passes through an RO membrane separation device, biological metabolites which have been generated by degradation of organic matter by microorganisms may cause the membrane surface of the RO membrane to be occluded, which results in a decrease in flux.

When the TOC-containing drainage directly passes through the RO membrane separation device without biological treatment, a high TOC concentration at which the drainage flows into the RO membrane separation device causes an environment in which microorganisms readily proliferate in the RO membrane separation device. Here, in order to inhibit biofouling in the RO membrane separation device, a slime-controlling agent is usually added to the TOC-containing drainage.

As the slime-controlling agent, a chlorine-based oxidizer such as inexpensive sodium hypochlorite has been widely used. However, this may cause a polyamide-based RO membrane to be deteriorated. As a slime-controlling agent which does not cause the RO membrane to be deteriorated, Japanese Patent Publication 2006-263510A describes a slime-controlling agent for membrane separation, the agent including a combined chlorine agent produced from a chlorine-based oxidizer and a sulfamic acid compound, and a slime-controlling agent for membrane separation, the agent containing a chlorine-based oxidizer and a sulfamic acid compound.

In addition, drainage drained from an electronic device factory may contaminate a nonionic detergent which attaches to the membrane surface of the RO membrane separation device and possibly decreases the flux. Consequently, the RO membrane separation treatment cannot be applied.

To solve such problems, a method and apparatus (Japanese Patent Publication 2005-169372A) has been disclosed. In the method and apparatus, when high-concentration and low-concentration organic-matter-containing water drained from an electronic device factory or other various fields are treated and collected by using the RO membrane separation device, biofouling and a decrease in flux due to the attachment of organic matter onto the membrane surface in the RO membrane separation device are prevented to carry out long-term stable treatment, and, simultaneously, high-quality treated water is yielded by efficiently decreasing the TOC concentration in water. As such technology, five-fold excess by weight or more of a scale inhibitor per calcium ion in organic-matter-containing water are added to the organic-matter-containing water, and an alkaline agent is added to the organic-matter-containing water before, after, or at the same time as the addition of the scale inhibitor to adjust pH to 9.5 or more, followed by RO separation treatment.

In addition, a method and apparatus (Japanese Patent No. 3906855) is known. In the method and apparatus, together with a scale inhibitor added, drainage whose pH is adjusted to 9.5 or more is subjected to activated carbon treatment and, then, RO membrane separation treatment. By performing these treatments, growth of microorganisms in an activated carbon tower and an RO membrane separation device is inhibited to stably yield treated water. In this method, the activated carbon tower is provided so as to absorb and remove an oxidizer mixed in raw water and organic matter contained in the raw water.

A predetermined amount of a scale inhibitor is added to water to be treated (hereinafter, referred to as "RO supply water") which is injected into an RO membrane separation device, and pH is adjusted to 9.5 or more. Then, the water passes through the RO membrane separation device. The above prevents biofouling and a decrease in the flux due to the attachment of organic matter onto the membrane surface in the RO membrane separation device to carry out long-term stable treatment, and high-quality treated water can be yielded by efficiently decreasing the TOC concentration in water.

Specifically, microorganisms cannot live in an alkaline range having a pH of 9.5 or more. In addition, a nonionic detergent that may decrease flux allows for detachment from the membrane surface in an alkaline range having a pH of 9.5 or more, thereby inhibiting attachment of this component onto the RO membrane surface.

By adding five-fold excess by weight or more of a scale inhibitor per calcium ion in RO supply water to the RO supply water, generation of scale is prevented.

There is a method in which five-fold excess by weight or more of a scale inhibitor per calcium ion in organic-matter-containing water is added to the organic-matter-containing water, and an alkaline agent is added to the organic-matter-containing water before, after, or at the same time as the addition of the scale inhibitor to adjust pH to 9.5 or more, followed by RO separation treatment. However, in this method, when a large amount of hardness components in raw water is present, addition of a scale dispersant is not sufficient for a scale-inhibiting effect. Accordingly, a cation-exchange tower or softening tower is provided to decrease the hardness load, and the pH is then required to be kept alkaline. In this case, Japanese Patent No. 3906855 describes that raw water is treated with an activated carbon tower, and is then subjected to treatment with a cation-exchange tower or softening tower, followed by treatment with an RO membrane separation device. In this treatment system, the cation-exchange tower or softening tower cannot be operated under highly alkaline conditions from a viewpoint of control of scale generation in the tower. Accordingly, the cation-exchange tower or softening tower and the activated carbon tower of the previous step should be operated under neutral conditions. As a result, the inside of the activated carbon tower and the cation-exchange tower or softening tower under the neutral conditions becomes a condition in which slime readily proliferates. This leads to a problem that biofilms detached from the tower cause the RO membrane separation device (or a safety filter of the RO membrane separation device) installed at a later step to be occluded.

In order to inhibit proliferation of slime, it is considered to add a disinfectant to raw water. However, as descried previously, a regular disinfectant such as sodium hypochlorite (NaClO) is largely removed in the activated carbon tower. Therefore, in the cation-exchange tower or softening tower following the step of the activated carbon tower, the sterilization effect cannot be achieved, and the proliferation of slime cannot be inhibited.

LIST OF DOCUMENTS

Patent Documents

Patent Document 1: Japanese Patent Publication H5-64782A
Patent Document 2: Japanese Patent Publication 2002-336886A
Patent Document 3: Japanese Patent Publication 2005-169372A
Patent Document 4: Japanese Patent No. 3906855
Patent Document 5: Japanese Patent Publication 2006-263510A

OBJECT AND SUMMARY OF INVENTION

Object of the Invention

It is an object of the present invention to solve problems described above and to provide a slime-controlling agent and a method for passing water through an activated carbon device which effectively inhibit slime in the whole part of an activated carbon layer of the activated carbon device. It is also an object of the present invention to provide a method and apparatus for treating organic-matter-containing water, the method and apparatus being capable of inhibiting growth of microorganisms in an activated carbon tower and a reverse osmosis membrane separation device to carry out long-term stable treatment in processes including activated carbon treatment and RO membrane separation treatment of a later step.

SUMMARY OF INVENTION

According to the first embodiment, a slime-controlling agent for activated carbon includes a combined chlorine agent produced from a chlorine-based oxidizer and a sulfamic acid compound.

According to the second embodiment, a method for passing water through an activated carbon device includes causing a slime-controlling agent according to the first embodiment to be present in water supplied to an activated carbon device or flushing water.

According to the third embodiment, a method for treating organic-mater-containing water includes the slime-controlling-agent-adding step of adding a slime-controlling agent to organic-matter-containing water; the activated-carbon-treating step of treating with activated carbon the organic-matter-containing water having undergone the slime-controllingagent-adding step; and the reverse-osmosis-membrane-separation step of passing the organic-matter-containing water having undergone the activated-carbon-treating step through means for reverse osmosis membrane separation, wherein the slime-controlling agent comprises a slime-controlling agent according to the first embodiment.

According to the fourth embodiment, a method for treating organic-matter-containing water further includes the hardness-component-removing step of decreasing hardness by passing the organic-matter-containing water having undergone the activated-carbon-treating step according to the third embodiment through means for cation exchange; the scale inhibitor-adding step of adding five-fold excess by weight or more of a scale inhibitor per calcium ion contained in the organic-matter-containing water having undergone the hardness-component-removing step to the organic-matter-containing water having undergone the hardness-component-removing step; and the pH-adjusting step of adjusting pH of the organic-matter-containing water to be injected into means for reverse osmosis membrane separation of a later step to 9.5 or more by adding an alkali to the organic-matter-containing water before, after, or at the same time as the scale inhibitor-adding step.

According to the fifth embodiment, an apparatus for treating organic-matter-containing water includes slime-controlling-agent-adding means for adding a slime-controlling agent to organic-matter-containing water; activated-carbon-treating means for treating with activated carbon the organic-matter-containing water having undergone the slime-controlling-agent-adding means; and reverse-osmosis-membrane-separation means for subjecting the organic-matter-containing water having undergone the activated-carbon-treating means to reverse osmosis membrane separation treatment, wherein the slime-controlling agent is a slime-controlling agent according to the first embodiment.

In the sixth embodiment, the apparatus for treating organic-matter-containing water according to the fifth embodiment further includes hardness component-removing means for providing cation-exchange means through which the organic-matter-containing water having undergone the activated-carbon-treating means passes; scale inhibitor-adding means for adding five-fold excess by weight or more of a scale inhibitor per calcium ion in the organic-matter-containing water having undergone the hardness-component-removing means to the organic-matter-containing water having undergone the hardness-component-removing means; and pH-adjusting means for adjusting pH of the organic-matter-containing water to be injected into means for reverse osmosis membrane separation of a later step to 9.5 or more by adding an alkali to the organic-matter-containing water before, after, or at the same time as the scale inhibitor-adding means.

Advantages of the Invention

A slime-controlling agent for activated carbon according to the present invention includes a combined chlorine agent produced from a chlorine-based oxidizer and a sulfamic acid compound, and inhibits proliferation of viable cells in an activated carbon device. In addition, this combined chlorine agent is not readily degraded and absorbed in contact with activated carbon, so that the agent easily passes through the activated carbon device. This prevents biofouling and a decrease in flux due to the attachment of organic matter onto the membrane surface in the RO membrane separation device of the step following the activated carbon device to carry out long-term stable treatment, and, simultaneously, high-quality treated water can be yielded by efficiently decreasing the TOC concentration in water. Further, the combined chlorine agent never or hardly exhibits an effect of deteriorating an RO membrane, so that the durability of the RO membrane remains good.

In addition, in the present invention, the pH of RO supply water is preferably adjusted to 9.5 or more by adding an alkali.

Specifically, microorganisms cannot live in an alkaline range. Because of this, adjusting pH of RO supply water to 9.5 or more enables an environment to be created, the environment having a nutritional source but preventing microorganisms from living. Accordingly, biofouling in the RO membrane separation device can be inhibited.

In addition, a nonionic detergent which may decrease flux detaches from the membrane surface in an alkaline range. Thus, adjusting the pH of the RO supply water to 9.5 or more can inhibit the attachment of this component onto the RO membrane surface.

In addition, in the present invention, five-fold excess by weight or more of a scale dispersant per calcium ion concentration in treated water after removal of hardness components is preferably added. The reasons for the above are described as follows.

Specifically, cation-exchange treatment can remove ions such as a calcium ion present in raw water, but the scale components present in the raw water may form a complex or may be suspended. Such substances are not removed by the cation-exchange treatment, and flow into the RO membrane separation device to become a core material which causes scale generation at the membrane surface. Here, addition of a scale inhibitor can inhibit growth of the core material for scale at the membrane surface and can completely inhibit troubles with the scale at the RO membrane surface. Under RO-operating conditions regarding RO supply water having a high pH of 9.5 or more, contamination of a tiny amount of the calcium ion generates scale such as calcium carbonate and causes the RO membrane to be occluded. Accordingly, five-fold excess by weight or more of a scale inhibitor per calcium ion in water after removal of hardness components is preferably added to the water to prevent generation of the scale.

BRIEF DESCRIPTION OF THE DRAWINGS

FIG. 3 is a graph showing a change over time in the concentration of chlorine leaked from an activated carbon tower when compared between Example 1 and Comparative Example 1.

DESCRIPTION OF EMBODIMENTS

Figure 1:
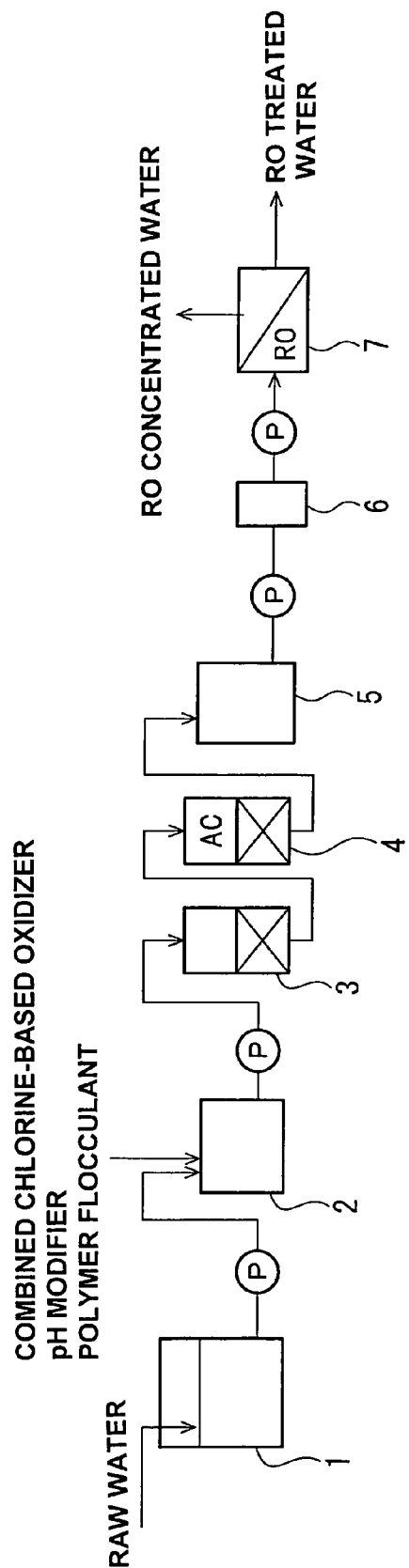
FIG. 1 is a systematic diagram showing a method and apparatus for treating organic-matter-containing water of an embodiment of the present invention.

Hereinafter, the present invention is further illustrated in detail.

First, a slime-controlling agent for activated carbon of the present invention is described in detail.

A slime-controlling agent for activated carbon of the present invention includes a combined chlorine agent produced from a chlorine-based oxidizer and a sulfamic acid compound.

Examples of the chlorine-based oxidizer used in the present invention can include, but are not limited to, chlorine gas, chlorine dioxide, hypochlorous acid or salts thereof, chlorous acid or salts thereof, chloric acid or salts thereof, perchloric acid or salts thereof, chlorinated isocyanuric acid or salts thereof, and the like. Among them, specific examples of the salts can include alkali metal hypochlorite such as sodium hypochlorite and potassium hypochlorite, alkali metal chlorite such as sodium chlorite and potassium chlorite, alkali metal chlorate such as ammonium chlorate, sodium chlorate, and potassium chlorate, alkaline earth metal chlorate such as calcium chlorate and barium chlorate, and the like. For these chlorine-based oxidizers, one kind can be used solely, or two kinds or more can be combined to be used. Among them, hypochlorous acid can be preferably used because they are easily handled.

As the sulfamic acid compound, examples can include a compound or a salt thereof, the compound represented by the following general formula [1]:

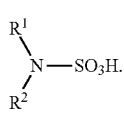

[1]

In the general formula [1], $R^1$ and $R^2$ each independently represent hydrogen or hydrocarbon having a carbon number of 1 to 8. As these sulfamic acid compounds, examples can include, in addition to sulfamic acid where both $R^1$ and $R^2$ are hydrogen, N-methyl sulfamic acid, N,N-dimethyl sulfamic acid, N-phenyl sulfamic acid, and the like. Examples of the salt of the sulfamic acid compound can include, alkali metal salts such as sodium salts and potassium salts, ammonium salts, guanidine salts, and the like. Specific examples can include sodium sulfamate, potassium sulfamate, and the like. For the sulfamic acid and sulfamate thereof, one kind can be used solely, or two kinds or more can be combined to be used.

When a chlorine-based oxidizer such as hypochlorite and a sulfamic acid compound such as sulfamate are blended, these compounds are combined to form chloro sulfamate and are stabilized. Without causing a difference in dissociation due to pH as for conventional chloramine or causing the resulting change in the concentration of free chlorine, these compounds enable the concentration of free chlorine to be kept stable in water.

In the present invention, the ratio of the chlorine-based oxidizer to the sulfamic acid compound is not particularly limited. However, the amount of the sulfamic acid compound per mol of effective chlorine in the chlorine-based oxidizer is preferably set to 0.5 to 5.0 mol, and more preferably 0.5 to 2.0 mol.

A slime-controlling agent for activated carbon of the present invention may contain, within a degree to which its effect is not impaired, an additional component other than a combined chlorine agent produced from a chlorine-based oxidizer and a sulfamic acid compound. Examples of the additional component can include alkaline agents, azoles, anionic polymers, phosphonates, and the like.

The alkaline agent is used for stabilizing the combined chlorine agent contained in the slime-controlling agent for activated carbon. Usually, sodium hydroxide or potassium hydroxide, etc., is used.

In the case of inclusion of the additional component, a dosage form of the slime-controlling agent for activated carbon of the present invention is not particularly limited. The dosage form can be a one-liquid type agent containing a combined chlorine agent produced from a chlorine-based oxidizer and a sulfamic acid compound, and one or more kinds selected from azoles, anionic polymers, and phosphonates. The dosage form can also be a two-liquid type agent in which the respective components are divided into two kinds of liquid. As the two-liquid type agent, examples can include, a two-liquid type agent containing solution A including a combined chlorine agent produced from a chlorine-based oxidizer and a sulfamic acid compound and solution B including additional components.

In the case of the one-liquid type agent, in order to maintain the stability of the combined chlorine agent, an alkali such as sodium hydroxide and potassium hydroxide is preferably added to adjust pH to 12 or more, and more preferably to adjust pH to 13 or more. In the case of the two-liquid type agent, the pH of the agent containing the combined chlorine agent is preferably similarly adjusted to 12 or more, and more preferably adjusted to 13 or more.

A method for passing water through an activated carbon device according to the present invention is to prevent slime-mediated damage by including such a slime-controlling agent for activated carbon of the present invention in water supplied to the activated carbon device or flushing water.

In this case, the concentration of the combined chlorine agent in water may be a degree to which an initial effect of preventing slime can be achieved. The concentration of the combined chlorine agent to be added is preferably, but is not particularly limited to, between 0.1 and 10 mg/L, and particularly between 1 and 5 mg/L. An activated carbon tower is suitable for the activated carbon device.

A slime-controlling agent of the present invention may be added to water flowing into the activated carbon device. Sodium hypochlorite may be added to the water flowing into the activated carbon device, and the slime-controlling agent of the present invention may be added to flushing water at the time of back washing. The latter can decrease the usage of the slime-controlling agent and can reduce the cost of the agent.

When an RO membrane device is provided in the step following the activated carbon device, a slime-controlling agent is preferably added to the water flowing into the activated carbon device as described in an embodiment of the following method and apparatus for treating organic-matter-containing water.

Hereinafter, by referring to the drawings, embodiments of a method and apparatus for treating organic-matter-containing water according to the present invention are described in detail.

Figure 2:
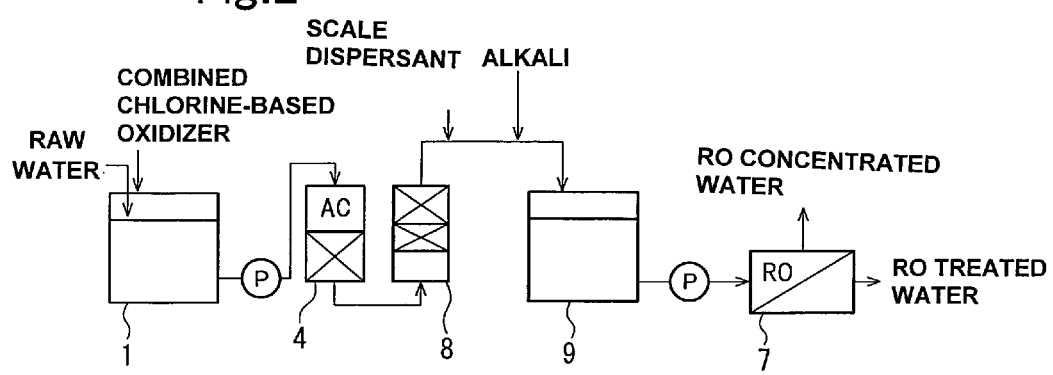
FIG. 2 is a systematic diagram showing a method and apparatus for treating organic-matter-containing water of another embodiment of the present invention.

FIGS. 1 and 2 are systematic diagrams showing embodiments of a method and apparatus for treating organic-matter-containing water according to the present invention. In figures, the symbol "P" denotes a pump.

In FIG. 1, in a flocculation tank 2, a slime-controlling agent for activated carbon of the present invention and a flocculant, and, if needed, a pH modifier are added to raw water (e.g., organic-matter-containing water such as industrial water) which is injected by way of a raw water tank 1. Then, the water passes through, in turn, a pressure filtration tower 3, an activated carbon tower 4, and filter-treatment water tank 5. After that, the water passes through a safety filter 6 and is injected into an RO membrane separation device 7 to be subjected to RO membrane separation treatment.

Examples of water exemplified include, but are not limited to, a variety of industrial water such as ground water and river water, and factory drainage such as drainage from processes for manufacturing a semiconductor device.

For the slime-controlling agent added, the concentration of the combined chlorine to be added is preferably 1 mg-$Cl_2$/L or more, and more preferably between 1 and 50 mg-$Cl_2$/L. In general, due to a poor ability of degradation and removal of the combined chlorine agent in the activated carbon, the agent immediately leaks from the activated carbon tower 4 of a later step to be able to achieve a sterilization effect. However, when the additive concentration is less than 1 mg-$Cl_2$/L or the flow SV in the activated carbon tower 4 is less than 20 $hr^{-1}$, the concentration at which the agent leaks from the activated carbon tower becomes markedly low. Then, slime sometimes grows in the activated carbon tower 4 or a device (e.g., a softening tower 8 of FIG. 2) installed at a later step. In addition, an excessively large amount of application of the combined chlorine agent markedly increases the cost of the agent, so that the concentration of the combined chlorine is preferably set to 50 mg-$Cl_2$/L or less.

In addition, in the case of presence of suspended matter in raw water, as shown in FIG. 1, after or before a slime-controlling agent is added, pH is adjusted to a pH range having optimal flocculation. Then, a flocculant is added and the suspended matter is removed beforehand by flocculation filtration, etc. After that, the water is preferably made to pass through the activated carbon tower. This means for flocculation filtration can be, but is not particularly limited to, any means capable of removing the suspended matter in the raw water by performing treatment such as pressure filtration, gravity filtration, microfiltration, ultrafiltration, pressurized flotation, and precipitation.

Examples of the activated carbon used in the activated carbon tower 4 include, but are not particularly limited to, coal-based one, coconut-shell-based one, and the like. Examples of the shape include, but are not particularly limited to, particulate activated carbon, spherical activated carbon, and the like.

Examples of the type of the activated carbon tower 4 include, but are not particularly limited to, a fluidized bed, an immobilized bed, and the like. In view of inhibition of leak of powdered coal, the immobilized bed is preferable.

The lower flow SV in this activated carbon tower 4 increases the amount of the combined chlorine agent which is removed by the activated carbon tower 4. Accordingly, the effect of inhibiting slime growth in a later step is lowered. Thus, the flow SV in the activated carbon tower 4 is preferably set to 20 $hr^{-1}$ or more. Provided that the flow SV in the activated carbon tower 4 is excessively high, the effect of removing an oxidizer, organic matter, and chromaticity, etc, which is derived from the raw water in the activated carbon tower 4 decreases. Accordingly, the flow SV in the activated carbon tower 4 is preferably set to, in particular, 50 $hr^{-1}$ or less, and especially between 20 and 40 $hr^{-1}$.

In FIG. 2, after a slime-controlling agent of the present invention and, if needed, a pH modifier are added to raw water which is injected by way of a raw water tank 1, the water is made to pass through, in turn, an activated carbon tower 4 and a softening tower 8. Then, five-fold excess or more of a scale dispersant per calcium ion concentration in water drained from the softening tower 8 (hereinafter, sometimes referred to as "softened treated water") is added. After that, an alkali is added to adjust pH to 9.5 or more. By way of an intermediate tank 9, the water is then injected into an RO membrane separation device 7 while keeping the high pH state to be subjected to RO membrane separation treatment.

In FIG. 2, the addition of the slime-controlling agent and the treatment in the activated carbon tower 4 are carried out in a manner similar to FIG. 1.

The ion-exchange resin used in the softening tower 8 can be any resin capable of removing hardness components in raw water, including, but being not particularly limited to, an H-type cation exchange resin whose ion exchange group is H, an Na-type cation exchange resin whose ion exchange group is Na, a chelating resin, and the like. In addition, examples of the type of the softening tower 8 include, but are not particularly limited to, a fluidized bed, an immobilized bed, and the like.

Besides, in the present invention, the treatment of removing hardness components is not limited to a softening tower, but a cation-exchange tower can be used. Further, the treatment is not limited to a tower type. However, in a manner similar to the activated carbon tower, the tower type is preferable from an aspect of treatment efficiency.

The flow SV in the softening tower 8 or cation-exchange tower is not particularly limited. From aspects of the treatment efficiency and the effect of removing hardness components, the treatment is usually carried out at the SV of between 10 and 40 $hr^{-1}$.

As a scale inhibitor which is added to treated water from the softening tower 8, a chelator-based scale inhibitor such as nitrilotriacetic acid (NTA) and ethylenediaminetetraacetic acid (EDTA) which readily forms a complex with a metal ion by dissociation in an alkaline range is preferably used. However, additional examples which can be used include (meth)acrylic acid polymers and salts thereof, low-molecular-weight polymers such as maleic acid polymers and salts thereof, ethylenediamine tetramethylene phosphonic acid and salts thereof, hydroxyethylidene diophosphonic acid and salts thereof, nitrilotris(methylene) phosphonic acid and salts thereof, phosphonic acid and phosphonate such as phosphonobutane tricarbonic acid and salts thereof, hexametaphosphoric acid and salts thereof, polymerized inorganic phosphoric acid and polymerized inorganic phosphate such as tripolyphosphoric acid and salts thereof, and the like. For these scale inhibitors, one kind can be used solely, or two kinds or more can be combined to be used.

The additive amount of the scale inhibitor is set to five-fold excess by weight or more per calcium ion concentration in water effluent from the softening tower 8 (i.e., water to which the scale inhibitor is added). When the additive amount of the scale inhibitor is less than five-fold excess by weight per calcium ion concentration in the softened treated water, a sufficient effect of adding the scale inhibitor cannot be achieved. Addition of an excessively large amount of the scale inhibitor is not preferable from an aspect of the cost of the agent. Accordingly, the amount is preferably set to between 5- and 50-fold excess by weight per calcium ion concentration in the softened treated water.

Next, to the water to which the scale inhibitor has been added is added an alkali. Then, the pH of the water (RO supply water) which is injected into the RO membrane separation device 7 of a later step is adjusted to 9.5 or more, preferably 10 or more, more preferably between 10.5 and 12, and, for example, between pH 10.5 and 11. The alkali used herein can be any inorganic-based alkaline agent capable of adjusting pH of the RO supply water to 9.5 or more, including, but being not particularly limited to, sodium hydroxide, potassium hydroxide, and the like.

The location at which the scale dispersant and the alkali are added can be any location between the softening tower 8 and the RO membrane separation device, and does not have any particular limitation. The order of adding these agents can be any order. However, in order to completely inhibit proliferation of microorganisms in the system and to completely inhibit scale generation in the system, preferably, the scale dispersant is added, and the alkali is then added to adjust pH of the RO supply water to 9.5 or more.

In the present invention, a reductant can be used as needed to degrade and remove the remaining combined chlorine agent by reduction treatment. The reductant used herein can be any reductant capable of removing the combined chlorine agent, including, but being not particularly limited to, sodium bisulfite and the like. For the reductant, one kind can be used solely, or two kinds or more can be combined to be used. The additive amount of the reductant can be an amount capable of completely removing the remaining combined chlorine agent. The reductant is usually added at the inlet side of the softening tower 8. However, the combined chlorine agent has a week effect of deteriorating an RO membrane. Thus, the degradation treatment for the combined chlorine agent by the reductant is usually unnecessary.

Examples of the RO membrane of the RO membrane separation device 7 as shown in FIGS. 1 and 2 include those having alkaline resistance such as, for example, a polyether amide composite membrane, a polyvinyl alcohol composite membrane, and an aromatic polyamide membrane. Preferably, the RO membrane uses a polyvinyl alcohol-based low-fouling RO membrane having a salt elimination capability in which a salt elimination rate at the RO membrane separation treatment of 1,500 mg/L of the sodium chloride solution under conditions of 1.47 MPa, 25° C., and pH 7 (hereinafter, simply referred to as the "salt elimination rate") is 95% or more. The preferable reasons for using such the low-fouling RO membrane are as follows.

Specifically, when compared to an aromatic polyamide membrane that is usually used, the above low-fouling RO membrane has no charge on the membrane surface and improves in hydrophilicity. Accordingly, the above is markedly superior in contamination resistance. However, for water containing a large amount of a nonionic detergent, the effect of the contamination resistance is reduced, and the flux decreases over time.

By adjusting pH of the RO supply water to 9.5 or more, the nonionic detergent which may decrease the RO membrane flux detaches from the membrane surface. Because of this, even if a typically employed aromatic polyamide membrane is used, a dramatic decrease in the flux can be inhibited. However, when the concentration of the nonionic detergent in the RO supply water is high, the foregoing effect decreases, which results in a decrease in the flux in a long term.

Here, the polyvinyl alcohol-based low-fouling RO membrane having the above specific salt elimination capability is used, and is preferably combined with conditions in which the RO supply water passes through at pH of 9.5 or more. Due to this, a long-term stable operation can be carried out without causing a decrease in the flux for the RO supply water containing a high concentration of the nonionic detergent.

The RO membrane can be any type such as a spiral type, a hollow-fiber type, and a tube type.

Next, to water which permeates through the RO membrane separation device (hereinafter, sometimes referred to as the "RO treated water") is added an acid to adjust pH to between 4 and 8. Further, the activated carbon treatment is carried out depending on the need. Then, the water is reused or released. Examples of the acid used herein include, but are not limited to, mineral acid such as hydrochloric acid and sulfuric acid.

The concentrated water in the RO membrane separation device 7 (hereinafter, sometimes referred to as the "RO concentrated water") is drained outside the system to be treated.

In addition, FIGS. 1 and 2 represent examples of an embodiment of the present invention. As long as does not exceed its purport, the present invention is not limited to those illustrated. For example, the treatment by the RO membrane separation device is not limited to one-step treatment, and can be multistep treatment having two steps or more. Furthermore, a mixing tank to adjust pH or to add a scale inhibitor, etc., can be provided.

EXAMPLES

Hereinafter, by referring to Examples and Comparative Examples, the present invention is more specifically described.

Example and Comparative Example of Embodiment Shown in FIG. 1

Example 1

To industrial water containing 1 mg/LasC of TOC was added, as a combined chlorine concentration, 5 mg-$Cl_2$/L of a slime-controlling agent including a combined chlorine agent produced from sodium hypochlorite and a sulfamic acid compound (specifically, sodium sulfamate) (a molar ratio of 1 mol of the sulfamine compound to effective chlorine is 1.5). Then, flocculation filtration treatment was carried out under conditions in which the additive amount of PAC (polyaluminum chloride) was 10 mg/L and the pH was 6. The flocculation filtration treated water was made to pass through an activated carbon tower under conditions at the SV of 20 $hr^{-1}$. Then, the water was made to pass through an RO membrane separation device (an ultralow-pressure aromatic polyamide-type RO membrane, "ES-20", manufactured by NITTO DENKO CORPORATION) under conditions at the flow volume of 60 L/hr and at the recovery rate of 80%. The pH of RO supply water was 5.5.

Comparative Example 1

Treatment was carried out under the conditions identical to those of Example 1, except that to industrial water containing 1 mg/LasC of TOC was added, as a combined chlorine concentration, between 8 and 10 mg-$Cl_2$/L of chloramine having a reaction product of sodium hypochlorite with ammonia.

In Example 1 and Comparative Example 1, the concentrations of the combined chlorine in water effluent from the activated carbon tower were determined. FIG. 3 showed the results.

As described in FIG. 3, Example 1 clearly demonstrated that chlorine leaked from the activated carbon tower in an early time point.

Example and Comparative Example of Embodiment Shown in FIG. 2

Example 2

To drainage containing a nonionic detergent and having the TOC concentration of 20 mg/L and the calcium concentration of 5 mg/L was added, as a combined chlorine concentration, 1 mg-Cl$_2$/L of the same slime-controlling agent as Example 1. Then, flocculation filtration treatment was carried out under conditions in which the additive amount of PAC (polyaluminum chloride) was 20 mg/L and the pH was 6.5. The flocculation filtration treated water was made to pass through an activated carbon tower of an immobilized bed type under conditions at the SV of 20 hr$^{-1}$, and the water was made to pass through a softening tower under conditions at the SV of 15 hr$^{-1}$. After that, 10 mg/L (i.e., five-fold excess by weight per calcium ion concentration of treated water from a softening tower) of a chelator-based scale inhibitor (Welclean A801, manufactured by Kurita Water Industries, Ltd.) was added, and NaOH was added to set pH to 10.5. After that, the RO membrane separation treatment was carried out by using an RO membrane separation device (an ultralow-pressure aromatic polyamide-type RO membrane, "ES-20", manufactured by NITTO DENKO CORPORATION) under conditions at the flow volume of 60 L/h and at the recovery rate of 80%. In addition, the pH of RO supply water was 9.5.

Comparative Example 2

Treatment was carried out in the conditions identical to those of Example 2, except that to drainage containing a nonionic detergent and having the TOC concentration of 20 mg/L and the calcium concentration of 5 mg/L was added, as a free chlorine concentration, 1 mg-Cl$_2$/L of NaClO instead of the above slime-controlling agent.

<Evaluation of Effect of Inhibiting Proliferation of Viable Cells>

For Example 2 and Comparative Example 2, the number of viable cells was investigated at the respective points. Table 1 showed the results.

TABLE 1

| Agent used | Example 2<br>Combined chlorine agent [1] | Comparative Example 2<br>NaClO |
|---|---|---|
| Activated carbon supply water | ND | ND |
| Activated carbon treated water | ND | 2.1 × 10$^5$ cells/mL |
| Softened treated water | ND | 1 × 10$^6$ cells/mL |
| RO supply water | ND | ND |
| RO concentrated water | ND | ND |

Note
[1] Combined chlorine agent: Combined chlorine agent produced from sodium hypochlorite and sodium sulfamate As clearly demonstrated in Table 1, in Example 2 in which a slime-controlling agent of a combined chlorine agent of the present invention had been used, no viable cells were observed at the all measurement points. In contrast, in Comparative Example 2, 210,000 cells/mL of viable cells were observed in the activated carbon treated water, and 1,000,000 cells/ml of viable cells were observed in the softening tower treated water.

<Estimation of Effect of Inhibiting Increase in Pressure Difference of RO Membrane>

In Example 2 and Comparative Example 2, a daily variation in a pressure difference between modules of the RO membrane separation device was investigated. Table 2 showed the results.

TABLE 2

| | Pressure Difference between Modules (MPa) | |
|---|---|---|
| Flow Days | Example 2 | Comparative Example 2 |
| 1 | 0.02 | 0.02 |
| 7 | 0.02 | 0.025 |
| 30 | 0.02 | 0.03 |
| 60 | 0.02 | 0.14 |

As clearly demonstrated in Table 2, in Example 2, no increase in the pressure difference between the modules of the RO membrane separation device was observed. In contrast, in Comparative Example 2, the pressure difference between the modules increased to 0.14 MPa after 60 days. Slime was detected in the occluded RO membrane.

The present invention has been described in detail by using specific embodiments. However, it is obvious to those skilled in the art that various modifications can be achieved without departing the spirit and scope of the present invention.

In addition, the present application claims the benefit of Japanese Patent Application 2009-046619 filed on Feb. 27, 2009, which is herein incorporated by reference in its entirety.

The invention claimed is:

1. A method for treating organic-matter-containing water, comprising:
 a slime-controlling agent preparation step of preparing a slime-controlling agent comprising a combined chlorine agent produced from a chlorine-based oxidizer and a sulfamic acid compound such that an amount of the sulfamic acid compound per mol of an effective chlorine in the chlorine-based oxidizer is 0.5 to 5.0 mol;
 a slime-controlling-agent adding step of adding the slime-controlling agent to organic-matter-containing water in a concentration of the combined chlorine agent between 0.1-10 mg-Cl$_2$/L;
 an activated-carbon-treating step of treating with activated carbon the organic-matter-containing water having undergone the slime-controlling-agent-adding step, the combined chlorine agent leaking in an activated carbon device to inhibit proliferation of viable cells in the activated carbon device; and
 a reverse-osmosis-membrane-separation step of passing the organic-matter-containing water having undergone the activated-carbon-treating step through a reverse osmosis membrane separation device comprising an aromatic polyamide membrane, the combined chlorine agent leaking in the activated carbon device further preventing biofouling and a decrease in flux due to an attachment of organic matter onto a membrane surface in a reverse osmosis membrane separation device.

2. The method according to claim 1, wherein the chlorine-based oxidizer is at least one selected from the group consisting of chlorine gas, chlorine dioxide, hypochlorous acid or salts thereof, chlorous acid or salts thereof, chloric acid or salts thereof, perchloric acid or salts thereof, and chlorinated isocyanuric acid or salts thereof.

3. The method according to claim 1, wherein the chlorine-based oxidizer is at least one of sodium hypochlorite and potassium hypochlorite.

4. The method according to claim 1, wherein the sulfamic acid compound is at least one selected from the group consisting of sulfamic acid, N-methyl sulfamic acid, N,N-dimethyl sulfamic acid, N-phenyl sulfamic acid, and salts thereof.

5. The method according to claim 1, wherein the sulfamic acid compound is at least one of sodium sulfamate and potassium sulfamate.

6. The method according to claim 1, further comprising, before or after the slime-controlling-agent adding step, a removing step of removing a suspended matter in the organic matter-containing-water by a filtration, the organic matter-containing-water after the removing step being supplied to the activated carbon device.

7. The method according to claim 6, wherein the removing step includes a step of adjusting pH in the organic matter-containing-water to optimize flocculation, a step of adding a flocculant to the organic matter-containing-water, and a step of removing the suspended matter.

8. The method according to claim 6, wherein the filtration is pressure filtration, gravity filtration, microfiltration, ultrafiltration, pressurized flotation, or precipitation.

9. A method for treating organic-matter-containing water, comprising:
- a slime-controlling-agent-adding step of adding a slime-controlling agent comprising a combined chlorine agent produced from a chlorine-based oxidizer and a sulfamic acid compound to organic-matter-containing water in a concentration of the combined chlorine agent between 1 and 50 mg-$Cl_2$/L;
- an activated-carbon-treating step of treating with activated carbon the organic-matter-containing water having undergone the slime-controlling-agent-adding step to inhibit proliferation of viable cells in an activated carbon device;
- a reverse-osmosis-membrane-separation step of passing the organic-matter-containing water having undergone the activated-carbon-treating step through a reverse osmosis membrane separation device, to prevent biofouling and a decrease in flux due to an attachment of organic matter onto a membrane surface in a reverse osmosis membrane separation device;
- a hardness-component-removing step of decreasing hardness by passing the organic-matter-containing water having undergone the activated-carbon-treating step through a cation-exchange device;
- a scale inhibitor-adding step of adding five-fold excess by weight or more of a scale inhibitor per calcium ion contained in the organic-matter-containing water having undergone the hardness-component-removing step to the organic-matter-containing water having undergone the hardness-component-removing step; and
- a pH-adjusting step of adjusting pH of the organic-matter-containing water to be injected into the reverse osmosis membrane separation device of a later step to 9.5 or more by adding an alkali to the organic-matter-containing water before, after, or at the same time as the scale inhibitor-adding step.

* * * * *